United States Patent [19]
Miyata et al.

[11] Patent Number: 5,968,788
[45] Date of Patent: *Oct. 19, 1999

[54] METHOD FOR PRODUCING FOLIC ACID

[75] Inventors: Reiko Miyata; Tetsu Yonehara, both of Aichi, Japan

[73] Assignee: Toray Industries, Inc., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/702,925

[22] Filed: Aug. 26, 1996

[30] Foreign Application Priority Data

Aug. 28, 1995 [JP] Japan .................................. 7-219197
Aug. 28, 1995 [JP] Japan .................................. 7-219198

[51] Int. Cl.$^6$ ........................... C12P 17/10; C12P 17/12; C12P 17/14; C12P 17/18
[52] U.S. Cl. .................. 435/119; 435/117; 435/120; 435/121; 435/122; 435/832; 435/837; 435/840; 435/921; 435/930; 435/940; 435/942
[58] Field of Search .................................. 435/119, 120, 435/121, 122, 117, 110, 822, 832, 837, 840, 911, 921, 930, 940, 942

[56] References Cited

U.S. PATENT DOCUMENTS 3,816,252 6/1974 Moran et al. ......................... 435/71.2
4,286,061 8/1981 Messing et al. ......................... 435/176

OTHER PUBLICATIONS

"Occurrence of *Crithidia* Factors and Folic Acid in Various Bacteria," by K. Iwai et al, *Journal of Bacteriology*, Oct. 1970, vol. 104, No. 1, pp. 197–201.

"The Production of Folic Acid by Microorganisms Isolated from Fermenting Corn Meal," by Fu Gen Yoa et al, *Kor. J. Appl. Microbiol. Bioeng.*, vol. 16, No. 5, 352–357 (1988).

Yoa et al—Kor. J. Appl. Microb. Bioeng –vol. 16, pp. 352–357, 1988.

Iwai et al.—J. Bacteriol., vol. 104, pp. 197–201, 1970.

Take. Niigata Igakkai Zasshi, vol. 84(3), pp. 204–212, 1970 Abstract.

Brock. Biology of Microorganisms, $3^{rd}$ ed., 1979, pp. 166 and 355.

Pelczar et al. Microbiology, $4^{th}$ ed., 1977, pp. 215 and 321.

Sagone et al. Free Radical Biol. and Med., vol. 14, pp. 27–35, 1993 Abstract.

The Condensed Chemical Dictionary, $10^{th}$ ed, 1981, p. 474.

*Primary Examiner*—Leon B. Lankford, Jr.
*Assistant Examiner*—Christopher R. Tate
*Attorney, Agent, or Firm*—Austin R. Miller

[57] ABSTRACT

Disclosed is a method for producing folic acid, comprising incubating yeast having the ability to produce folic acid of 0.3 mg or more or incubating bacteria having the ability to produce folic acid of 1 mg or more per liter of the culture, thereby accumulating folic acid in the culture.

9 Claims, No Drawings

METHOD FOR PRODUCING FOLIC ACID

TECHNICAL FIELD

The present invention relates to a method for producing folic acid.

BACKGROUND ART

Folic acid as referred to herein includes all substances having folic acid activities and shall not be limited to only pteroylglutamic acid (hereinafter referred to as PteGlu) which is generally said to be folic acid in the narrow sense of the word. In addition to PteGlu, it includes, for example, pteroyl-poly-γ-glutamic acid (hereinafter referred to as Pte-Glun with n=from 2 to 8), tetrahydrofolic acid, 5-formyl-tetrahydrofolic acid, 10-formyl-tetrahydrofolic acid, 5-methyl-tetrahydrofolic acid, etc.

At present, PteGlu of folic acids is industrially produced through chemical synthesis. Briefly, three components of 2,4,5-triamino-6-hydroxypyrimidine, 1,1,3-trichloroacetone and p-aminobenzoylglutamic acid are condensed in the presence of sodium nitrite in a solution of sodium acetate to give a crude product of folic acid, PteGlu, and the product is purified through recrystallization.

There are some reports disclosing that bacteria of the genera Pseudomonas, Micrococcus, Gluconobacter, Corynebacterium, Aeromonas and Bacillus produce a minor amount (from several tens to one hundred and several tens μg/liter) of a substance having folic acid activities in their cultures (see J. of Bacteriol., 104, 197–201 (1970); Kor. J. Appl. Microbiol. Bioeng., (16), 5, 352 (1988)).

A conventional method for producing folic acid through chemical synthesis is known, in which, however, the raw materials to be used are expensive and the yield of the product is low. Therefore, it is difficult to say that the method is advantageous. As has been mentioned hereinabove, there are some reports disclosing that several species of bacteria produce a substance having folic acid activities in their cultures, but the amount of the substance to be produced is extremely small. Therefore, the proposals disclosed are problematic in that they could not be directly led to the industrial production of the substance.

DISCLOSURE OF THE INVENTION

The present invention relates to a method for producing folic acid, comprising incubating yeast having the ability to produce folic acid or incubating bacteria having the ability to produce folic acid of 1 mg or more per liter of the culture, thereby accumulating folic acid in the culture.

In addition, it also relates to a method for producing folic acid, comprising using microorganisms in the presence of para-aminobenzoic acids.

BEST MODES OF CARRYING OUT THE INVENTION

Folic acid as referred to herein includes all substances having folic acid activities or, that is, those having biological activities to be quantitatively determined through the growth of folic acid-requiring strains of lactic acid bacteria, *Lactobacillus rhamaasus* ATCC 7469, *Streptococcus faecalis* ATCC 8043 and *Pediococcus cerevisiae* ATCC 8081. For example, as substances having folic acid activities, there are mentioned pteroylglutamic acid (hereinafter referred to as PteGlu) which is generally said to be folic acid in the narrow sense of the word, pteroyl-poly-γ-glutamic acid (hereinafter referred to as PteGlun with n=from 2 to 8), tetrahydrofolic acid, 5-formyl-tetrahydrofolic acid, 10-formyl-tetrahydrofolic acid, 5-methyl-tetrahydrofolic acid, etc.

In the present invention, preferably used are yeasts belonging to the genera Candida, Yarrowia, Hansenula, Torulopsis, Saccharomyces and Pichia and bacteria belonging to the genera Bacillus, Rhodococcus and Brevibacterium.

For example, such yeasts include *Candida famata* ATCC 10536, *Candida guilliermondii* ATCC 9058, *Yarrowia lipolytica* ATCC 20226, *Saccharomyces cerevisiae* ATCC 26108, *Pichia glucozyma* ATCC 18938, *Candida glabrata* ATCC 15126, *Yarrowia lipolytica* ATCC 20225, etc.; and such bacteria include *Bacillus subtilis* ATCC 19219, *Bacillus megaterium* ATCC 19218, *Rhodococcus equi* ATCC 21280, *Brevibacterium ammoniagenes* ATCC 6872, etc. Of these, preferably used are yeasts of *Candida famata* ATCC 10539, *Candida guilliermondii* ATCC 9058, *Yarrowia lipolytica* ATCC 20225, *Hansenula glucozyma* ATCC 18938, *Candida glabrata* ATCC 15126 and *Saccharomyces cerevisiae* ATCC 26108, and bacteria of *Bacillus subtilis* ATCC 19219 and *Bacillus megaterium* ATCC 19218.

The bacteria to be used in the present invention shall have the ability to produce folic acid of 1 mg or more, preferably 1.5 mg or more, per liter of their culture. The producing ability can be quantitatively determined by measuring the biological activity that shall be based on the growth of a folic acid-requiring strain, *Streptococcus faecalis* ATCC 8043, according to the method described in Vitamins and Coenzymes, the last volume, pp. 385–388 (published by Tokyo Kagaku Dojin Co.). Briefly, a test liquid is added to a medium having the composition mentioned below, the amount of the test liquid added being the same as that of the medium, and then cells of the folic acid-requiring strain mentioned above are inoculated onto the medium and incubated therein at 37° C. After 24 hours, the amount of the cells thus grown in the medium is measured. This is compared with the amount of the cells of *Streptococcus faecalis* ATCC 8043 as grown in a medium containing pteroylglutamic acid, which is the standard control.

| Casein hydrolysate | 50 mg | $FeSO_4 \cdot 7H_2O$ | 0.1 mg |
|---|---|---|---|
| L-tryptophan | 1 mg | $MnSO_4 \cdot 4H_2O$ | 0.1 mg |
| L-cysteine hydrochloride | 8 mg | NaCl | 0.1 mg |
| L-asparagine | 1 mg | Thiamine hydrochloride | 5 μg |
| Adenine sulfate | 0.1 mg | Riboflavin | 5 μg |
| Guanine hydrochioride | 0.1 mg | Nicotinic acid | 10 μg |
| Xanthine | 0.1 mg | Biotin | 0.04 μg |
| Uracil | 0.1 mg | Calcium pantothenate | 5 μg |
| Sodium acetate | 200 mg | P-aminobenzoic acid | 1 μg |
| Glucose | 200 mg | Pyridoxine hydrochloride | 2 μg |
| Polysorbate 80 | 10 mg | Pyridoxal hydrochioride | 5 μg |
| $KHPO_4$ | 30 mg | Pyridoxamine dihydrochloride | 2 μg |
| $MgSO_4 \cdot 7H_2O$ | 2 mg | Ascorbic acid | 10 mg | weight/10 ml (medium)

The yeasts to be used in the present invention are not specifically defined but are preferably those having the ability to produce folic acid of 300 μg or more per liter of their culture, which shall be measured in accordance with the method mentioned above.

To incubate such yeasts in accordance with the method of the present invention, suitably used are media that contain carbon sources to. be assimilated by the yeasts, nitrogen sources to be assimilated by them, other inorganic salts and minor elements. The carbon sources include saccharides such as glucose, sucrose, maltose, etc.; organic acids such as acetic acid, lactic acid, fumaric acid, etc.; alcohols such as methanol, ethanol, propanol, etc.; and oils and fats such as glycerin, soybean oil, etc. The nitrogen sources include inorganic and organic nitrogen compounds such as ammonium sulfate, ammonium nitrate, ammonium chloride, urea, peptone, meat extract, corn steep liquor, aqueous ammonia, etc. The inorganic salts include potassium phosphate, sodium phosphate, magnesium sulfate, and also iron, manganese and other metal components. If desired, the media may contain minor elements such as vitamins, amino acids, nucleic acids, etc. Also if desired, they may contain surfactants. Glutamic acid or its derivatives (from 0.01 to 5%) is preferably further added. More specifically, glutamic acid, sodium glutamate and potassium glutamate are more preferably used.

In the method of the present invention, in general, yeasts are incubated advantageously under aerobic conditions. The incubation may be conducted generally at from 15 to 40° C., preferably at from 20 to 35° C., and at a pH of from 2 to 10, preferably from 3 to 8, for from 1 to 10 days, preferably from 3 to 6 days.

To incubate bacteria according to the method of the present invention, suitably used are media that contain carbon sources to be assimilated by the bacteria, nitrogen sources to be assimilated by them, other inorganic salts and minor elements.

The carbon sources include saccharides such as sucrose, maltose, glucose, etc.; organic acids such as acetic acid, lactic acid, fumaric acid, succinic acid, malic acid, etc.; and oils and fats such as glycerin, soybean oil, etc.

The nitrogen sources include inorganic and organic nitrogen compounds such as ammonium sulfate, ammonium nitrate, ammonium chloride, urea, aqueous ammonia, peptone, corn steep liquor, ajieki, yeast extract, etc. The inorganic salts include potassium phosphate, sodium phosphate, magnesium sulfate, and also iron, manganese and other metal components. If desired, the media may contain minor elements such as vitamins, amino acids, nucleic acids, etc. Glutamic acid or its derivatives (from 0.01 to 5%) is preferably further added. More specifically, glutamic acid, sodium glutamate and potassium glutamate are more preferably used.

In the method of the present invention, in general, bacteria are incubated advantageously under aerobic conditions. The incubation may be conducted generally at from 15 to 40° C., preferably at from 25 to 37° C., and at a pH of from 5 to 10, preferably from 6 to 9, for from 1 to 12 days, preferably from 3 to 7 days.

The present invention also provides a method for producing folic acid, comprising using microorganisms in the presence of para-aminobenzoic acids. The microorganisms to be used in this method are not specifically defined but preferably include, for example, mold, actimomycetes, yeasts and bacteria. In addition to these, glutamic acid-producing microbes are also preferably used. The yeasts may be those belonging to the genera Torulopsis Yarrowia, Saccharomyces, Hansenula and Candida. Of these, preferred are *Candida famata, Candida guilliermondii, Yarrowia lipolytica, glucozyma, Candida glabrata* and *Saccharomyces cerevisiae*. The bacteria may be those belonging to the genera Bacillus, Rhodococcus and Brevibacterium. Of these, preferred are *Bacillus subtilis, Bacillus megaterium, Rhodococcus equi* and *Brevibacterium ammoniagenes*.

As mentioned hereinabove, the microorganisms to be used for producing folic acid in the presence of p-aminobenzoic acids, but preferred are bacteria having the ability to produce folic acid of 1 mg or more per liter of their culture, and yeasts having the ability to produce folic acid of 300 μg or more per liter of their culture.

The p-aminobenzoic acids to be added to the media where the microorganisms are incubated may be any ones capable of substantially exhibiting the activity of p-aminobenzoic acid (PABA) as one of vitamins, and concretely include p-aminobenzoic acid as well as alkali metal salts thereof such as potassium p-aminobenzoate and sodium p-aminobenzoate, and esters of p-aminobenzoic acid such as methyl p-aminobenzoate, ethyl p-aminobenzoate and butyl p-aminobenzoate.

The amount of the p-aminobenzoic acids to be added shall be from 0.01% to 5% (by weight/amount of liquid), preferably from 0.1% to 2% (by weight/amount of liquid), in terms of the free acid. These can be added all at a time or intermittently in portions.

The cultures thus obtained and the cell extracts from them can be directly added to feed and others as folic acid sources. If desired, folic acid can be isolated from them. To extract folic acid from them, any conventional method can be employed advantageously. For example, employable are the methods described in Methods of Vitamin Experiments III (page 304 and the following pages) (published by Tokyo Kagaku Dojin Co., in 1985). The folic acid as produced in the cultures partly exists in the form of its γ-polyglutamic acid derivatives. Therefore, when the folic acid existing in the cells incubated is measured, it is desirable to pre-treat the cells with a conjugase so as to hydrolyze the polyglutamic acid moiety, thereby converting PteGlun into PteGlu, prior to the measurement.

To isolate folic acid compounds from the culture supernatants and to isolate folic acid from the cell extracts, any ordinary method for isolating folic acid can be employed (see Method of Vitamin Experiments III, pp. 304–309). For example, employable are a method of fractionation using DEAE-cellulose, QAE-Sephadex A-25, Sephadex G-15 or G-25, and a partitioning method through high-performance liquid chromatography.

To detect and quantitatively determine folic acid compounds, employable are bioassay using lactic acid bacteria, and high-performance liquid chromatography using a thin-layer chromatography, ion-exchanging chromatography or reversed-phase exchanging chromatography column as combined with an UV detector or fluorescence detector.

The folic acid as obtained according to the present invention can be used as a tonic agent in medicines, raw materials for medicines and processed, powdery milk compounds, as an additive to feed for domestic animals, and as an additive to be used in incubation of microorganisms.

EXAMPLES

Next, the present invention is described in more detail with reference to the following examples, which, however, are not intended to restrict the scope of the invention. The cells used in the following examples were obtained from ATCC (American Type Culture Collection).

Example 1

Test tubes (diameter: 18 mm) each were filled with 3 ml of a medium (pH 6.0) composed of 5% glucose, 0.3% monopotassium phosphate, 0.5% ammonium sulfate, 0.3% sodium glutamate, 0.05% magnesium sulfate and 0.3% calcium carbonate and then sterilized. One platinum loop of the cells as shown in Table 1 below, which had been grown on a slant, glucose-peptone-agar medium, were inoculated in the medium in each test tube. These were incubated therein at 30° C. for 75 hours by shaking culture. The cultures each were centrifuged, and the total folic acid content of each supernatant was measured through microbiological determination. The results obtained are shown in Table 1.

TABLE 1

| Strain | Total Folic Acid Content(*) (mg/liter) |
|---|---|
| Candida famata ATCC 10539 | 4.0 |
| Candida quilliermondii ATCC 9058 | 2.0 |
| Yarrowia lipolytica ATCC 20225 | 3.5 |
| Hansenula glucozyma ATCC 18938 | 1.5 |
| Candida glabrata ATCC 15126 | 3.1 |
| Sacchharomyces cerevisiae ATCC 26108 | 5.0 |

(*)Total folic acid content: This was obtained as follows:

The sample liquid to be measured was added to a medium having the composition mentioned below, the amount of the sample liquid added being the same as that of the medium, and then cells of a folic acid-requiring strain, *Streptococcus faecalis* ATCC 8043 were inoculated in the medium and incubated therein at 37° C. After 24 hours, the amount of the cells thus grown in the medium was measured. This was compared with the amount of the cells of *Streptococcus faecalis* ATCC 8043 as grown in a medium containing pteroylglutamic acid, which is the standard control.

| | | | |
|---|---|---|---|
| Casein hydrolysate | 50 mg | FeSO$_4$.7H$_2$O | 0.1 mg |
| L-tryptophan | 1 mg | MnSO$_4$.4H$_2$0 | 0.1 mg |
| L-cysteine hydrochloride | 8 mg | NaCl | 0.1 mg |
| L-asparagine | 1 mg | Thiamine hydrochloride | 5 μg |
| Adenine sulfate | 0.1 mg | Riboflavin | 5 μg |
| Guanine hydrochloride | 0.1 mg | Nicotinic acid | 10 μg |
| Xanthine | 0.1 mg | Biotin | 0.04 μg |
| Uracil | 0.1 mg | Calcium pantothenate | 5 μg |
| Sodium acetate | 200 mg | P-aminobenzoic acid | 1 μg |
| Glucose | 200 mg | Pyridoxine hydrochloride | 2 μg |
| Polysorbate 80 | 10 mg | Pyridoxal hydrochioride | 5 μg |
| KHPO$_4$ | 30 mg | Pyridoxamine dihydrochloride | 2 μg |
| MgSO$_4$.7H$_2$0 | 2 mg | Ascorbic acid | 10 mg | weight/10 ml (medium)

Example 2

Two test tubes (diameter: 18 mm) were prepared for each strain mentioned in Table 2 below, each filled with 3 ml of a medium (pH 6.0) composed of 6% glucose, 0.3% monopotassium phosphate, 1.0% ammonium sulfate, 0.05% magnesium sulfate and 0.3% calcium carbonate, and then sterilized. one platinum loop of the cells as shown in Table 2, which had been grown on a slant, glucose-peptone-agar medium, were inoculated onto the medium in each test tube. These were incubated therein at 30° C. for 24 hours by shaking culture. After the incubation for 24 hours, sodium para-aminobenzoate (PABA.Na), that had been separately sterilized, was added to one test tube of each strain to have a concentration of 0.5%, and the cells in these test tubes were further incubated for additional 75 hours. To the other test tube, the salt was not added, and the cells were further incubated for additional 75 hours. The culture in each test tube was centrifuged, and the total folic acid content of the supernatant was measured through microbiological determination. The results obtained are shown in Table 2.

TABLE 2

| Strain | Total Folic Acid Content (*) (mg/liter) PABA.Na added. | Total Folic Acid Content (*) (mg/liter) PABA.Na not added. |
|---|---|---|
| Candida famata ATCC 10539 | 22.1 | 2.6 |
| Candida guilliermondii ATCC 9058 | 12.3 | 2.9 |
| Yarrowia lipolytica ATCC 20225 | 13.5 | 2.1 |
| Hansenula glucozyma ATCC 18938 | 5.7 | 0.5 |
| Candida glabrata ATCC 15126 | 13.9 | 0.3 |
| Saccharomyces cerevisiae ATCC 26108 | 11.1 | 2.1 |

PABA.Na: Sodium para-aminobenzoate
(%): The total folic acid content was measured in the same method as described in Example 1.

Example 3

Test tubes (diameter: 18 mm) each were filled with 3 ml of a medium (pH 7.5) composed of 5% sucrose, 0.3% monopotassium phosphate, 0.5% ammonium sulfate, 0.3% sodium glutamate, 0.05% magnesium sulfate and 0.3% calcium carbonate, and then sterilized. One platinum loop of the cells as shown in Table 3 below, which had been grown on a slant, peptone-agar medium, were inoculated onto the medium in each test tube. These were incubated therein at 30° C. for 68 hours by shaking culture. The cultures each were centrifuged, and the total folic acid content of each supernatant was measured through microbiological determination. The results obtained are shown in Table 3.

TABLE 3

| Strain | Total Folic Acid Content(*) (mg/liter) |
|---|---|
| Bacillus subtilis ATCC 19219 | 3.9 |
| Bacillus megaterium ATCC 19218 | 1.8 |

(*): The total folic acid content was measured in the same method as described in Example 1.

Example 4

The same experiments as in Example 2 were carried out, except that test tubes (diameter: 18 mm) each were filled with 3 ml of a medium (pH 7.5) composed of 6% sucrose, 0.5% sodium glutamate, 0.3% monopotassium phosphate, 1.0% ammonium sulfate, 0.05% magnesium sulfate and 0.3% calcium carbonate, and then sterilized, and that one platinum loop of the cells as shown in Table 4 below, which had been grown on a slant, peptone-agar medium, were inoculated onto the medium in each test tube. The results obtained are shown in Table 4.

TABLE 4

| Strain | Total Folic Acid Content(*) (mg/liter) PABA.Na added. | Total Folic Acid Content(*) (mg/liter) PABA.Na not added. |
| --- | --- | --- |
| Bacillus subtilis ATCC 19219 | 21.0 | 2.3 |
| Bacillus megaterium ATCC 19218 | 12.3 | 1.9 |
| Rhodococcus equi ATCC 21280 | 6.0 | 2.5 |
| Brevibacterium ammoniagenes ATCC 6872 | 8.9 | 2.1 |

PABA.Na: Sodium para-aminobenzoate
(*): The total folic acid content was measured in the same method as described in Example 1.

Example 5

500 ml of a medium having the same composition as in Example 2 was put into each of ten 5-liter Erlenmeyer flasks and sterilized. Next, one platinum loop of cells of *Candida guilliermondii* ATCC 9058 were inoculated onto the medium in each flask and incubated therein at 30° C. for 35 hours by shaking culture. After the incubation for 35 hours, para-aminobenzoic acid that had been separately sterilized was added to each medium to have a concentration of 0.5%. Then, the incubation was further conducted for additional 85 hours. Each culture was centrifuged. The resulting supernatants were combined to be 2.3 liters. 250 g of active charcoal (Hakutaka, produced by Takeda Chemicals Co.) was added thereto and stirred at room temperature for 1 hour. Then, this was filtered under suction. The resulting active charcoal residue was suspended in one liter of an aqueous solution of 50-% ethanol/5-% aqueous ammonia (9/1), then stirred at room temperature for 1 hour, and filtered under suction. The resulting filtrate was evaporated to obtain 500 ml of a concentrate. Next, this concentrate was fractionated through a HPLC column C18SG120 (30×250 mm) (produced by Shiseido Co.) to collect a fraction containing a larger amount of pteroylglutamic acid. This fraction was adjusted at a pH of 2.0 by adding 2-N sulfuric acid thereto, then crystallized through evaporation, and filtered to obtain 3 mg of a crystal. The infrared absorption spectrum of the crystal was measured, and the purity thereof was measured through high-performance liquid chromatography as using fluorescence detector (excitation wavelength: 360 nm, fluorescence wavelength: 455 nm) to be 88.5%.

INDUSTRIAL APPLICABILITY

According to the present invention, it is possible to efficiently produce compounds with folic acid activities which can be utilized as a tonic agent in medicines, raw materials for medicines and processed, powdery milk compounds, as an additive to feed for domestic animals, and as an additive to be used in incubation of microorganisms.

We claim:

1. A method for producing folic acid comprising:
   a) culturing a yeast species selected from the group consisting of *Candida famata, Candida guilliermondii, Yarrowia lipolytica, Pichia glucozyma*, and *Saccharomyces cerevisiae*, in a culture medium at a temperature of about 20–35° C., at a pH of about 3–8, for about 3–6 days, said culture medium containing 5% sugar selected from the group consisting of glucose, fructose, sucrose, and maltose, wherein said yeast produces at least 0.3 mg of folic acid per liter of said culture medium, and
   b) recovering accumulated folic acid from said culture medium.

2. The method for producing folic acid as claimed in claim 1, further comprising adding para-aminobenzoic acid to the culture medium.

3. The method for producing folic acid as claimed in claim 2, wherein said para-aminobenzoic acid is at least one selected from the group consisting of potassium para-aminobenzoate, sodium para-aminobenzoate, methyl para-aminobenzoate, ethyl para-aminobenzoate and butyl para-aminobenzoate.

4. A method for producing folic acid comprising:
   a) culturing a bacterial species of a genera selected from the group consisting of Bacillus, Brevibacterium and Rhodococcus, in a culture medium at a temperature of about 25–37° C., at a pH of about 6–9, for about 3–7 days, in the presence of p-aminobenzoic acid in an amount of 0.01%–5% by weight/amount of liquid, expressed as free acid, said culture medium containing 5% sugar selected from the group consisting of glucose, fructose, sucrose, and maltose, wherein said bacteria produce at least 1 mg of folic acid per liter of said culture medium, and
   b) recovering accumulated folic acid from said culture medium.

5. The method for producing folic acid as claimed in claim 4, wherein said bacterial species is selected from the group consisting of *Bacillus subtilis* and *Bacillus megaterium*.

6. A method for producing folic acid comprising:
   (a) culturing yeast selected from the group consisting of *Candida famata* ATCC 10536, *Candida guilliermondii* ATCC 9058, *Yarrowia lipolytica* ATCC 20226, *Saccharomyces cerevisiae* ATCC 26108, *Hansenula glucozyma* ATCC 18938, *Candida glabrata* ATCC 15126 and *Yarrowia lipolvtica* ATCC 20225 in a culture medium, for a suitable time under appropriate conditions, wherein said yeast produces at least 300 μg folic acid per liter of said culture medium; and
   (b) recovering accumulated folic acid from said culture medium.

7. The method according to claim 6, further comprising adding para-aminobenzoic acid to said culture medium.

8. The method for producing folic acid as claimed in claim 7, wherein said para-aminobenzoic acid is at least one selected from the group consisting of potassium para-aminobenzoate, sodium para-aminobenzoate, methyl para-aminobenzoate, ethyl para-aminobenzoate and butyl para-aminobenzoate.

9. A method for producing folic acid comprising:
   (a) culturing bacteria selected from the group consisting of *Bacillus subtilis* ATCC 19219, *Bacillus megaterium* ATCC 19218, *Rhodococcus equi* ATCC 21280, and *Brevibacterium ammoniagenes* ATCC 6872 in a culture medium in the presence of p-aminobenzoic acid in an amount of 0.01%–5% by weight/amount of liquid, expressed as free acid, for a suitable time under appropriate conditions, wherein said bacteria produce at least 1 mg folic acid per liter of culture medium; and
   (b) recovering accumulated folic acid from said culture medium.

* * * * *